United States Patent
Wood et al.

(10) Patent No.: US 7,869,565 B2
(45) Date of Patent: Jan. 11, 2011

(54) CLASSIFICATION METHOD FOR SEDIMENTARY ROCKS

(75) Inventors: Rachel Wood, Edinburgh (GB); Andrew Curtis, Edinbugh (GB); Andreas Kayser, London (GB)

(73) Assignee: Schlumberger Technology Corporation, Cambridge, MA (US)

(*) Notice: Subject to any disclaimer, the term of this patent is extended or adjusted under 35 U.S.C. 154(b) by 364 days.

(21) Appl. No.: 11/579,688

(22) PCT Filed: May 6, 2005

(86) PCT No.: PCT/GB2005/001800

§ 371 (c)(1),
(2), (4) Date: Oct. 6, 2008

(87) PCT Pub. No.: WO2005/108965

PCT Pub. Date: Nov. 17, 2005

(65) Prior Publication Data

US 2009/0103677 A1    Apr. 23, 2009

(30) Foreign Application Priority Data

May 12, 2004    (GB) .................................. 0410589.6

(51) Int. Cl.
*G01N 23/06* (2006.01)
(52) U.S. Cl. ....................................................... 378/53
(58) Field of Classification Search .................... 378/53
See application file for complete search history.

(56) References Cited

U.S. PATENT DOCUMENTS

| 4,669,299 A | 6/1987 | Closmann |
| 4,722,095 A | 1/1988 | Muegge et al. |
| 4,982,086 A | 1/1991 | Withjack |
| 5,036,193 A | 7/1991 | Davis, Jr. et al. |
| 2003/0231017 A1 | 12/2003 | Kiesl et al. |

OTHER PUBLICATIONS

Taylor et al., "Diamonds: time capsules from the Siberian Mantle", Chemie der Erde—Geochemistry, vol. 64, Issue 1, (Mar. 30, 2004), pp. 1-74.*
Al-Hanai et al. 'Carbonate Rocks', SCAweb.org. The Society of Core Analysts. pp. 1-10. Date Accessed: Apr. 11, 2007. http://www.sca.web.org/assets/pdf/scal-2000_carbonates-.pdf.
Choquette and Pray 'Geologic nomenclature and classification of porosity in sedimentary carbonates' AAPG Bulletin, 1970, vol. 54(2), pp. 207-250.
Duliu 'Computer axial tomography in geosciences: an overview' Earth Science Reviews, 1999, vol. 48, pp. 265-281.

(Continued)

*Primary Examiner*—Chih-Cheng G Kao
(74) *Attorney, Agent, or Firm*—Vincent Loccisano; James McAleenan; Brigid Laffey

(57) ABSTRACT

A method of determining a parameter of interest of reservoir rock formation is described using the steps of measuring an x-ray attenuation or absorption distribution of a sample of said rock formation, identifying the mineral phase part of said distribution, and subdividing the mineral phase part of said distribution to derive classification or rock type information of said sample.

6 Claims, 6 Drawing Sheets

OTHER PUBLICATIONS

Dunham 'Classification of carbonate rocks according to depositional texture' in 'Classification of carbonate rocks- a symposium' Tulsa: The American Association of Petroleum Geologists, ed. Ham, vol. 1, (1962): pp. 108-121.

Hicks et al 'Distribution of residual oil in heterogenous carbonate cores using x-ray ct' SPE Formation Evaluation, 1992, vol. 7(3), pp. 235-240.

Hidajat 'Study of vuggy carbonates using x-ray CT scanner and nmr' SPE 77396, 2002.

Knackstedt et al 'Digital core laboratory: properties of reservoir core derived from 3D images' SPE 87009, 2004.

Lucia 'Petrophysical parameters estimated from visual description of carbonate rocks: a field classification of carbonate pore space' Journal of Petroleum Technology, Mar. 1983, pp. 629-637.

Midttun & Giertsen 'Petroleum applications of virtual reality technology: Introducing a new paradigm' 68th Annual International Meeting: Society of Exploration Geophysics, Expanded Abstracts, 1998.

Oh & Lindquist 'Image thresholding by indicator kriging.' IEEE Transactions on pattern analysis and machine intelligence, vol. 21(7), (1999): p. 590-602.

Ramakrisham et al 'A model based interpretation methodology for evaluating carbonate reservoirs' SPE 71704, 2001.

Russell et al 'Rock types and permeability prediction from dipmeter and image logs: Shuaiba reservoir (Aptian), Abu Dhabi' AAPG Bulletin, vol. 86(10), (2002): pp. 1709-1732.

\* cited by examiner

CLASSIFICATION METHOD FOR SEDIMENTARY ROCKS

The present invention generally relates to methods of classifying sedimentary rocks, such as carbonates. More specifically, the invention relates to the use of x-ray attenuation or absorption to derive a classification of samples into reservoir rock types.

BACKGROUND OF THE INVENTION

The economic value of an oil and gas bearing formation depends on the amount of producible hydrocarbons contained in the subsurface reservoir. This amount of producible hydrocarbons is a function of the formation porosity and permeability.

NMR measurements for formation evaluation yield signals originating from the precessing protons of the fluids in the pore space of the rock. Due to interactions of the fluid molecules with each other or the pore walls, the signal of each proton decays exponentially with a characteristic time T 2 (longitudinal relaxation time).

Permeability is a function of, among other things, the T 2 distribution and the pore size distribution. In sandstones, where porosity and permeability is regular, this relationship is fairly consistent and NMR is a reliable method of characterizing reservoirs. Carbonate reservoirs porosity and permeability are not so well defined as sandstone and the relationship varies with different lithofacies.

Siliciclastic sediments, such as sandstones and shale, develop through the attrition of other rocks. Their grains are sorted prior to deposition. Sandstones and shale are formed of sedimentary particles derived from sources outside the depositional basin. Siliciclastic sediments are relatively stable after deposition. As a result, the pore space in sandstones is mainly intergranular and its complexity depends on the degree of sorting.

Carbonates form in special environments and, in contrast to sandstones, are biochemical in nature. They are essentially autochthonous, as they form very close to the final depositional sites. They are not transported and sorted in the same way as sandstones. Carbonates are usually deposited very close to their source and develop as a result of various processes. Their texture is more dependent on the nature of the skeletal grains than on external influences. Intrabasinal factors control facies development. Reefs, bioherms, and biostroms are example of in-place local deposition where organisms have built wave-resistant structures above the level of adjacent time-equivalent sediments.

Carbonates are characterized by different types of porosity and have unimodal, bimodal, and other complex pore structure distributions. This distribution results in wide permeability variations for the same total porosity, making it difficult to predict their producibility. In this case, long echo trains with a large number of echoes and a long-pre-polarization time may be applicable. Carbonate rock texture produces spatial variations in permeability and capillary bound water volumes.

Carbonates are particularly sensitive to post-depositional diagenesis, including dissolution, cementation, recrystallization, dolomitization, and replacement by other minerals. Calcite can be readily dolomitized, sometimes increasing porosity. Complete leaching of grains by meteoric pore fluids can lead to textural inversion which may enhance reservoir quality through dissolution or occlude reservoirs quality through cementation. Burial compaction fracturing and stylolithification are common diagenetic effects in carbonates, creating high-permeability zones and permeability barriers or baffles, respectively. Diagenesis can cause dramatic changes in carbonate pore size and shape. On a large scale, porosity due to fracturing or dissolution of carbonate rocks can produce "pores" up to the size of caverns.

Given the wide range of origins for carbonate rocks, and the variety of secondary processes which may affect them, it is not surprising that the convoluted pore space of a carbonate may be quite different from that found in siliciclastic sediments. All carbonate sediments are composed of three textural elements: grains, matrix, and cement.

In general, geologists have attempted to classify sedimentary rocks on a natural basis, but some schemes have genetic implications, i.e., knowledge or origin of a particular reservoir rock type (RRT) is assumed.

The relative proportions of the components, among others, can be used to classify carbonate sediments. A widely used classification scheme is proposed by Dunham (see Dunham, "Classification of carbonate rocks according to depositional texture", in *Classification of carbonate rocks—A Symposium*, Ham, ed., volume 1, pages 108-121. AAPG Mem., 1962.) In Dunham, carbonates are classified based on the presence or absence of lime mud and grain support. Textures range from grainstone, rudstone, and packstone (grain-supported) to wackestone and mudstone (mud-supported). Where depositional texture is not recognizable, carbonates are classified as boundstone or crystalline. Within these carbonates, the porosity takes many forms, depending on the inherent fabric of the rock and on the types of processes that can occur during and after deposition.

In many carbonates, it is not possible to map the rock texture using conventional logs. Rock texture exerts a strong influence on permeability variations and bound water distributions—important factors in reservoir simulations. For example, while porosity logs may show little change between grainstones, wackestones and mudstones, the capillary-bound water volumes and permeabilities for these rocks may be very different.

Another classification system, by Lucia (see Lucia, Petrophysical parameters estimated from visual description of carbonate rocks: a field classification of pore space. Journal of Petroleum Technology, 35:626-637, March 1983) is based on petrographical attributes and porosity. Dolomites are included in this classification scheme.

Pore type characterization is used in a classification scheme of Choquette & Pray (see P. W. Choquette and L. C. Pray. Geologic nomenclature and classification of porosity in sedimentary carbonates. AAPG Bull., 54:207-250, 1970). Choquette & Pray, in contrast to Dunham, classify carbonates according to fabric and nonfabric pore types. Examples of the former are inter- and intraparticle porosity, while those of the latter are fractures and vugs. Another classification scheme, by Melim et al., differentiates between primary and secondary pore spaces using the description based on classification of Choquette & Pray. Some of the petrographical information obtained using these classifications is used to improve the petrophysical evaluation of the geological formations.

NMR logging tools use large magnets to strongly polarize hydrogen nuclei in water and hydrocarbons as they diffuse about and are contained in the pore space in rocks. When the magnet is removed, the hydrogen nuclei relax. The relaxation time, T 2, depends on the pore-size distribution; larger pores typically have longer relaxation times. Tar and viscous oils relax more quickly than light oil and water. The variations in relaxation time produce a T2 distribution from which fluid components and pore sizes are interpreted. As is well known to those versed in the art, T1, and T2 distributions correlate very well if the diffusion is negligible.

Two standard permeability equations have been established for applications in the oil industry. The Schlumberger-Doll Research (SDR) equation uses simply the geometric mean of the measure T 2 distribution to derive permeability. The Timur-Coates equation uses a T2 cutoff value that divides the T2 distribution into a movable and an irreducible fluid saturation and relates these values to permeability. Other permeability models such as the Kozeny-Carman method may also be used for permeability determination.

Various methods have been proposed to determine formation properties of carbonates using Nuclear Magnetic Resonance. Hidajat et al. (see Hidajat et al., "Study of Vuggy Carbonates using x-ray CT Scanner and NMR", SPE 77396, 2002) works to improve correlation between NMR T 2 response in carbonate systems, including the contributions of vugs to carbonate permeability. Ramakrishnan et al. (see Ramakrishnan et al., "A Model-based Interpretation Methodology for Evaluating Carbonate Reservoirs", SPE 71704, 2002) develops an integrated methodology for carbonate interpretation. The methodology of Ramakrishnan parametrizes the pore structure in terms of a multiporosity system of fractures, vugs, inter- and intragranular porosities. NMR data is useful in separating the inter- and intragranular components. The method of Ramakrishnan requires the use of more services than are normally run to provide data.

A summary of the problems in characterizing the properties of carbonate rocks authored by W. Al-Hanai et al is published by the Society of Core Analysts under the title "Carbonate Rocks". The published U.S. patent application 2003/0231017 provides a summary of the state of art for correlating NMR data with classification of carbonate rocks.

X-ray based analysis of core sample, including computer tomography and Micro-CT instruments, are used in both academia (e.g. O. G. Duliu, "Computer axial tomography in geosciences: an overview." *Earth-Science Reviews*, 48, 265-281, 1999; M. A. Knackstedt et al. "Digital Core Laboratory: Properties of reservoir core derived from 3D images" SPE 87009 (2004) and the oil industry (e.g., J, P. Hicks et al., "Distribution of residual oil in heterogeneous carbonate cores using x-ray ct." SPE Formation Evaluation, 293, 235 ff.) to provide high resolution images and data of sedimentary rocks in 1, 2 or 3D at a micron-scale, so enabling discrimination of pore-size distribution, as well as facilitating the study of multiphase fluid flow within such porous media.

In the light of the above prior art, it is seen as an object improved methods of classifying sedimentary rocks for interpreting log and seismic data.

SUMMARY OF THE INVENTION

A method is proposed that creates a virtual 1, 2, or 3D image, and data derived thereof, of any sedimentary rock (siliclastic, evaporite, carbonate, or organic) using data derived from a tomogram, such as a micro-CT. The tomogram includes parts that represent the pore space phase and parts that represent the mineral phase. The method allows the detection, distinction and segmentation of different components within the mineral phase due to differences in x-ray density (i.e. due to different mineralogies, crystallographies, or porosity distributions, particularly below the tomogram resolution. This enables distinction of different inorganic and organic grain types, cements, and matrix, in particular within carbonate rocks. In turn, quantification of these geological components enables the categorization of rock samples into various classification schemes, including Reservoir Rock Type (RRT) schemes, based on 1, 2 or 3D data.

It has not previously been realized that discrimination between sedimentary rock components that share the same mineralogy, but differ in their distribution of porosity below that of the resolution of the tomogram, is also possible and can be used to define classes of rock based on their constituent components. Through subdivision of the mineral phase related tomogram, it is possible to classify the rock types of samples and use these rock types for the evaluation of log data, such as porosity measurements, and of seismic data.

The method includes the steps of

Generating x-ray tomograms of one or more rock samples. The sample size is arbitrary and may range from cuttings to core or core plug samples. The tomogram resolution is preferably chosen such that pore space part or phase is easily distinguishable from the mineral parts or phases.

Subdividing the tomogram into pore space phase and mineral phases.

Sub-divide mineral phase tomographic data into any number of components on the basis of differences in x-ray attenuation, as for example may be caused by differences in density. These will include components of different mineralogy, microporosity distribution (that is distribution of porosity below the resolution of the tomogram data) such as different grain types (organic and inorganic), cements, and matrix.

Derive pertinent statistics or properties of any desired components, including of the pore phase, where these statistics or properties may be resolved on the basis of the tomogram. Pertinent statistics or properties include relative volume of different components, statistical variation of properties over different scales, spatial arrangement of properties, parameters to describe pore size distribution, and connectivity, variations in diagenetic overprinting, texture, grain size and sorting.

The information derived in steps above, possibly augmented with other data, can be used for further evaluation of the rock and/or reservoir by, for example defining a set of rock classes that are discriminated at least in part by the information; or identifying the rock class corresponding to each sample using a pre-existing set of rock classes.

The sub-division into distinct components with the same mineralogy is made using micro-tomography x-ray density data due to differences in density is caused by differences in porosity or crystallography that are below the resolution of the tomogram.

The method can be applied as part of a reservoir rock typing scheme.

Once a rock sample is classified or its rock type is established, it can be used to increase the accuracy of other measurements such as log measurements or seismic measurements and their interpretation.

These and other aspects of the invention will be apparent from the following detailed description of non-limitative examples and drawings.

EXAMPLES

Figure 1:
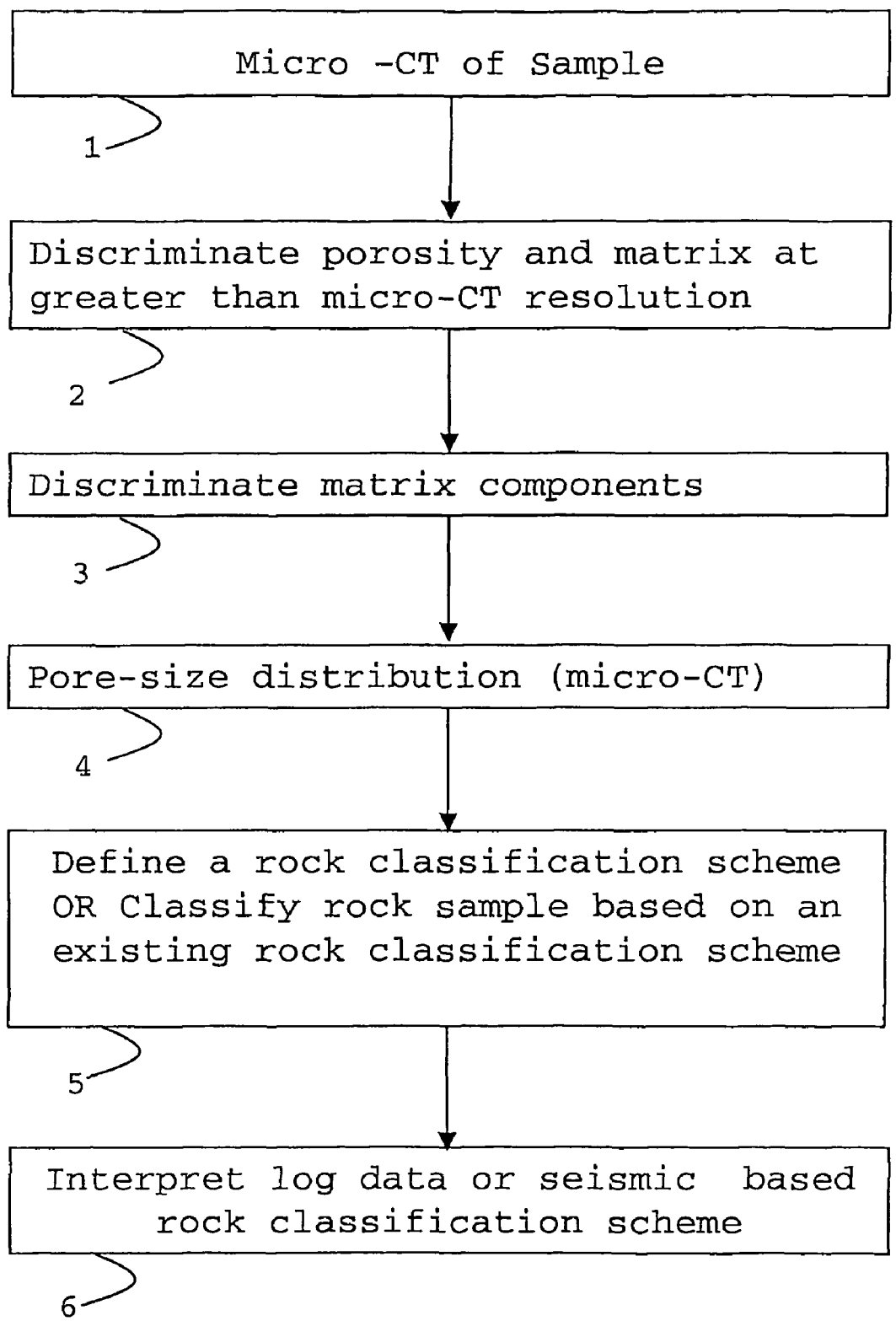
FIG. 1 is a flow diagram illustration steps in accordance with an example of the invention.

Examples of the steps in accordance with the invention are shown in FIG. 1. Each step is described below in greater detail.

In step 1, 1D, 2D, or 3D x-ray tomogram of one or more rock samples are generated. This may be done using any micro-CT facility, including bench-top devices, bespoke micro-CT systems, and synchrotron micro-tomography.

Figure 2A:
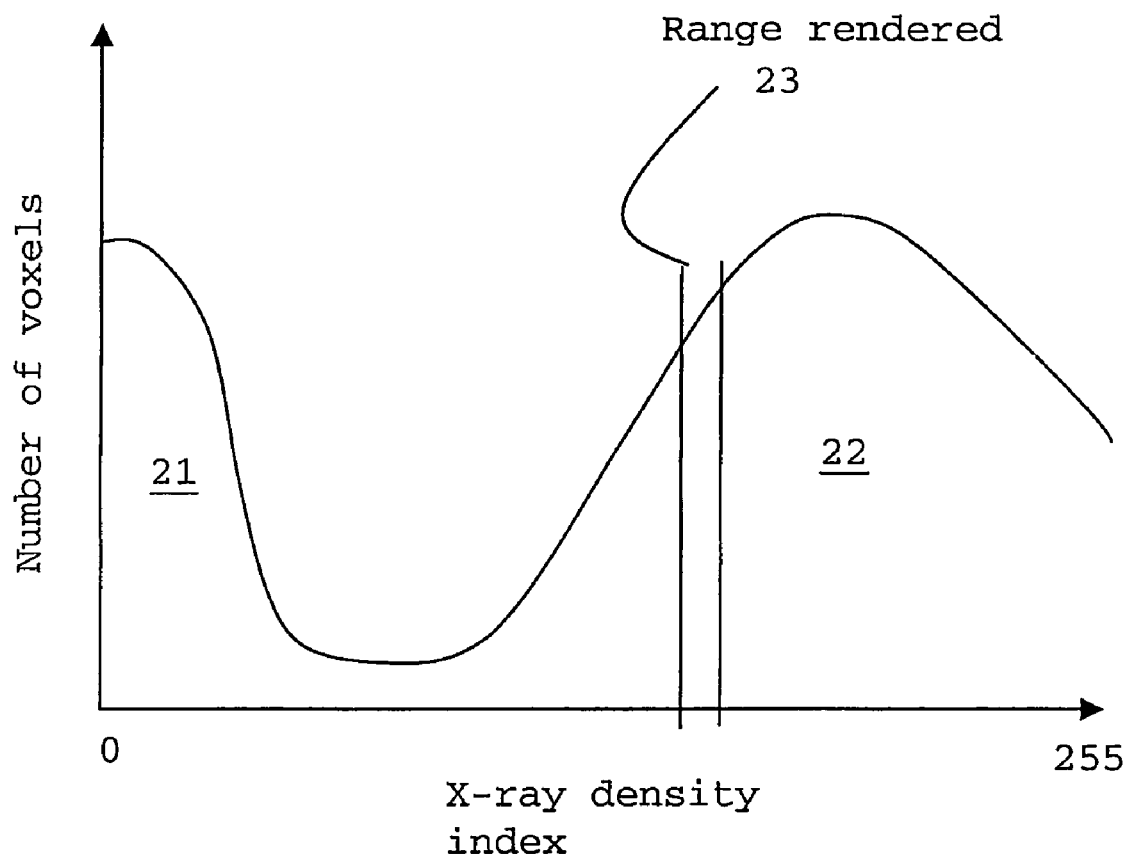
FIG. 2A is a schematic distribution plot over x-ray attenuation.

As an example, an x-ray tomogram of a portion of 4 inch diameter carbonate core was generated, to 165 μm resolution, and tomograms of various sub-samples therefrom where also created to a resolution of 17 μm. The tomograms were produced by acquiring a series of radiographs at different viewing angles around 360°. The micro-CT images had up to 889×889×765 voxels. The camera used acquires radiographs of 1024 pixels with a depth per pixel of 8 bits. The computer tomography (μCT) images were digitised and voxel values from the original sample were calculated using a grey scale and assigned an 8-bit value (0-255) relating to attributes. As a result a x-ray density or attenuation plot versus distribution was generated as schematically shown in FIG. 2A. An example slice through the tomogram is shown in the larger section of FIG. 2B.

In Step 2, the tomogram is subdivided into pore phase and mineral phases using any suitable methodology using for example the methodology of W. Oh and B. Lindquist, "Image thresholding by indicator kriging. Transactions on Pattern Analysis and Machine Intelligence, IEEE, 0.21 (1999), 590-602.

The normalized intensity distributions generated show distinct peaks that correspond to pores phase 21 and the matrix (mineral or solid) phase 22 as shown in FIG. 2A. The effect of low-density pore inclusions and voxels spanning both pore and mineral phases, however, leads to a spread in the low-density signal, such that it is impossible to unambiguously differentiate between the pores and mineral phases. This requires a clear and consistent method to label each voxel as either pore, or grain, and to further allow differentiation of different grain types. One method of phase separation can be made through detection and localisation of edges between different phases. The edge-based kriging algorithm of Oh and Lindquist was used, but the invention is not limited to this particular methodology. The kriging algorithm involved the choice of 2 cutoff attenuation coefficients lying near the peaks.

Once the volume file was created, data were visualized and analyzed using commercially available image rendering software (Inside Reality™) that allows stereo viewing of pore space in 3D. The use of such Virtual Reality software offers the possibility to view slices of the rock samples in any direction, and also allows both slice and transparent volume views are possible (an example of such a transparent volume view within the whole core tomogram is shown on the left of FIG. 2B).

In step 3, the mineral phase data is subdivided into any number of components on the basis of differences in x-ray attenuation due to differences in mineralogy, crystallography or density. FIG. 2A illustrates one range 23 of attenuation values forming a subdivision. The mineral phase peak 22 can be subdivided into an arbitrary number of such ranges. The result of the subdivision allows to differentiate between low- and high-Mg calcite, dolomite, clay, anhydrite, chert and quartz, as well as accessory minerals such as phosphates, glauconite, ankerite, siderite, feldspars and pyrite, etc., as well as those components of differing microporosity distribution such as different carbonate grain types (skeletal, organic, and inorganic), cements, and matrix. It should be noted that the differentiation is based on or caused by properties of the material which are below the resolution of the tomogram itself.

The rock can then be classified, for example, by segregating those parts of the rock that occupy different parts of the density spectrum or visual inspection using for example a thin slice. After inspection the slice can be placed at the correct location in the tomogram and the attenuation/density of the identified parts of the slice can be used to gage the attenuation of the same parts in the other section of the tomogram. Alternatively, known control samples of particular components within the tomogram can be included in the capture of the tomogram to automatically determine density values that correspond to each such component.

Differences in x-ray density values for each finite cube volume (voxel) of the sample allow two types of fossil to be distinguished: discrimination of the 3D spatial distribution of two major low-Mg skeletal components of the sample, rudist bivalve shells and miliolinid foraminiferal was possible. These can be distinguished by taking two different narrow bands of the density spectrum. An example of the narrow band corresponding to rudist densities, and the corresponding 3D distribution of rudist shell fragments in a portion of the tomogram, are shown in FIG. 2B.

From the components identified through the range in the density spectrum they occupy, it is possible (Step 4) to derive pertinent statistics or properties, including of the pore phase, where these statistics or properties may be resolved on the basis of the tomogram (e.g., relative volume of different components, statistical variation of properties over different scales, spatial arrangement of properties, parameters to describe pore size distribution, and connectivity, variations in diagenetic overprinting, texture, grain size and sorting).

Figure 2B:
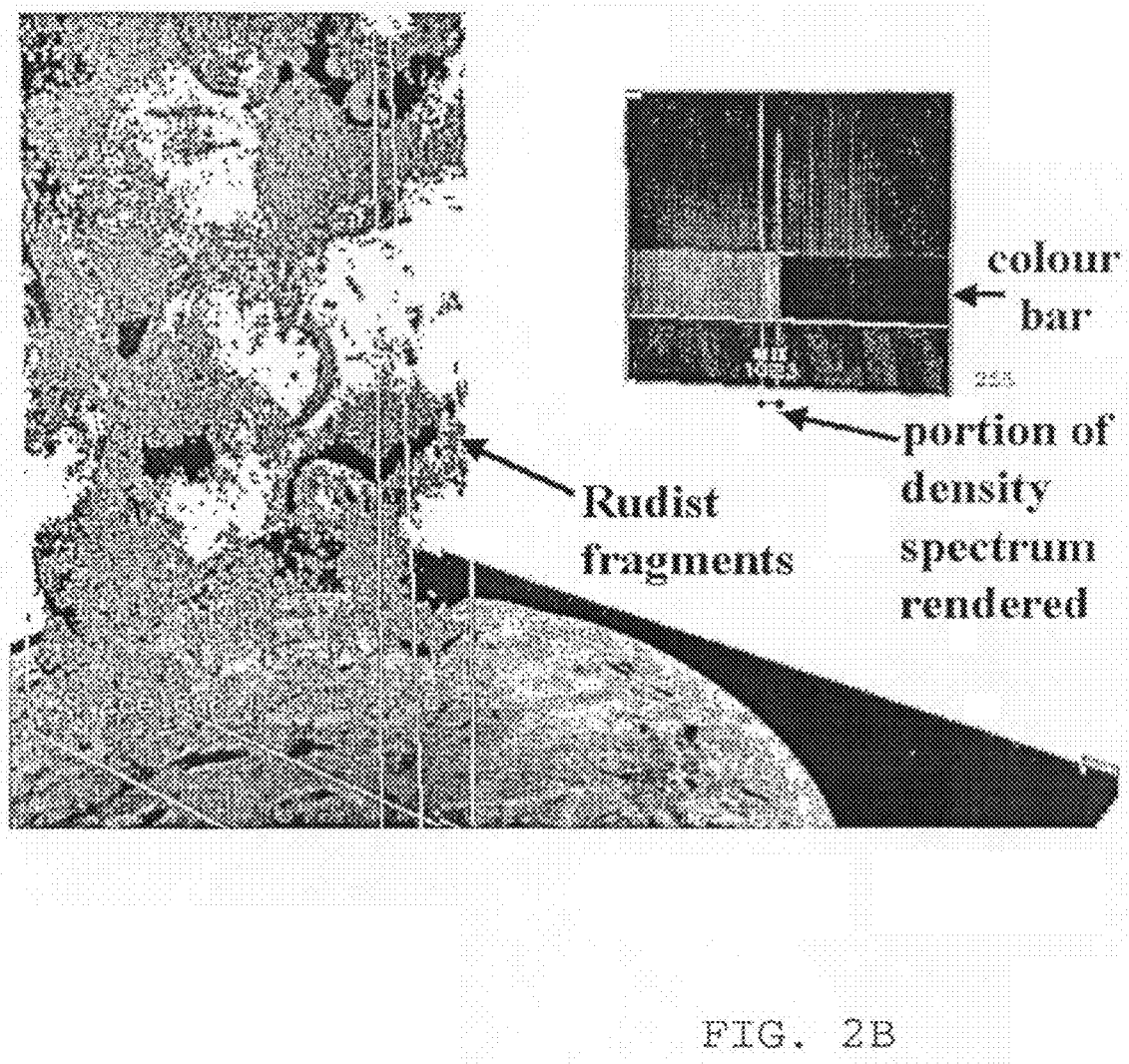
FIG. 2B is the rendering (visualization) of a part of a rock sample having a pre-selected attenuation range.

Pertinent statistics of the various depositional components of the sample were derived, together with a 3D spatial visualisation of each component and are shown in FIG. 2B. The sample had a total porosity of 23% (determined by laboratory fluid flow tests). It contained 12% rudists and 1.2% miliolinid foraminiferans where the latter two were determined from the micro-tomograph.

Once the information derived in steps 1-4 is available, and possibly augmented with other data (e.g., petrophysical measurements made on each rock sample, or well logs taken at the same depth as the core from which each sample was taken, it can be used to either (Step 5):

define a set of rock classes that are discriminated at least in part by the information provided by steps 1-4 above (e.g., see Table 1); or identify the rock class corresponding to each sample using a pre-existing set of rock classes (e.g., into one of the two classes in Table 1.

Table 1 shows classification of rock classes, with the sample examined being automatically assigned to the class "Rudist Floatstone".

TABLE 1

| Rock class: Rudist Floatstone | Rock class: Fossiliferous wackestone | Further Rock classes. |
|---|---|---|
| Volume Porosity 20-30% Volume Rudists 10-20% Volume miliolinids 0.5-2.5% | Volume Porosity 10-15% Volume Rudists 0-1% Volume miliolinids 1-5% | |

Figure 3:
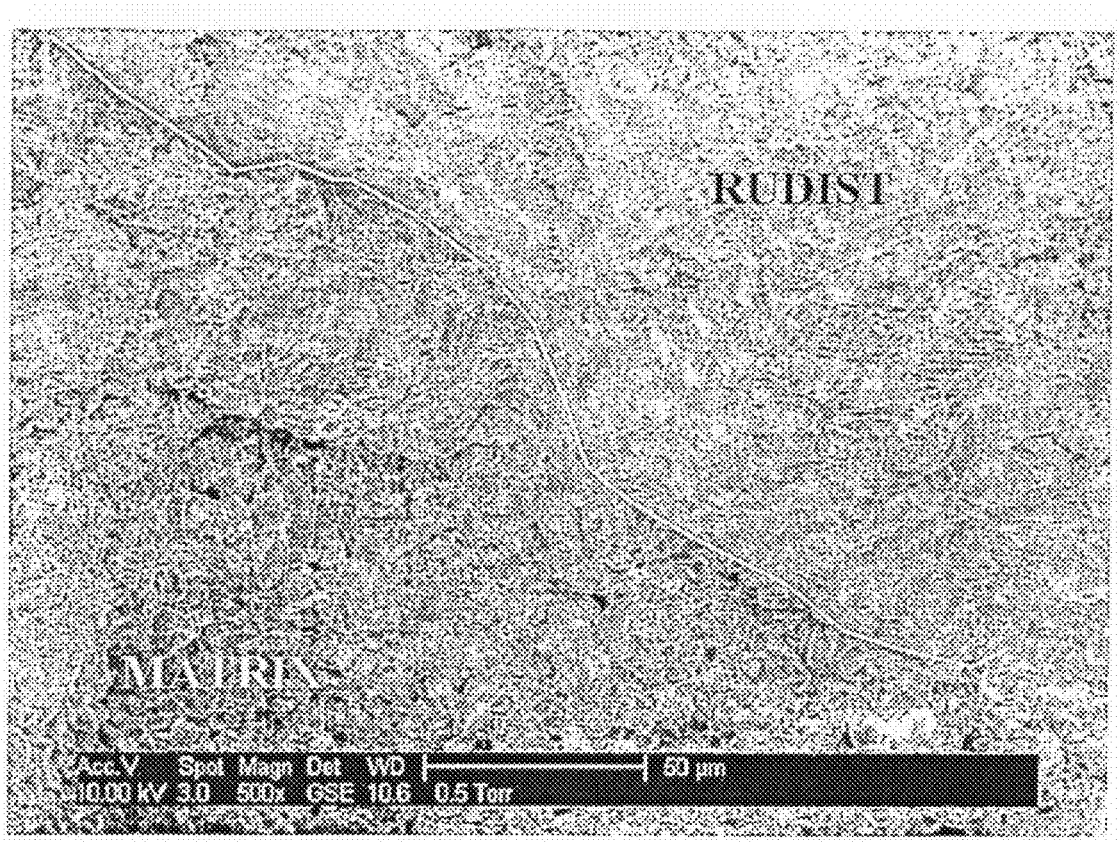
FIG. 3 is a scanning electron microscopic (SEM) image.
Figure 4:
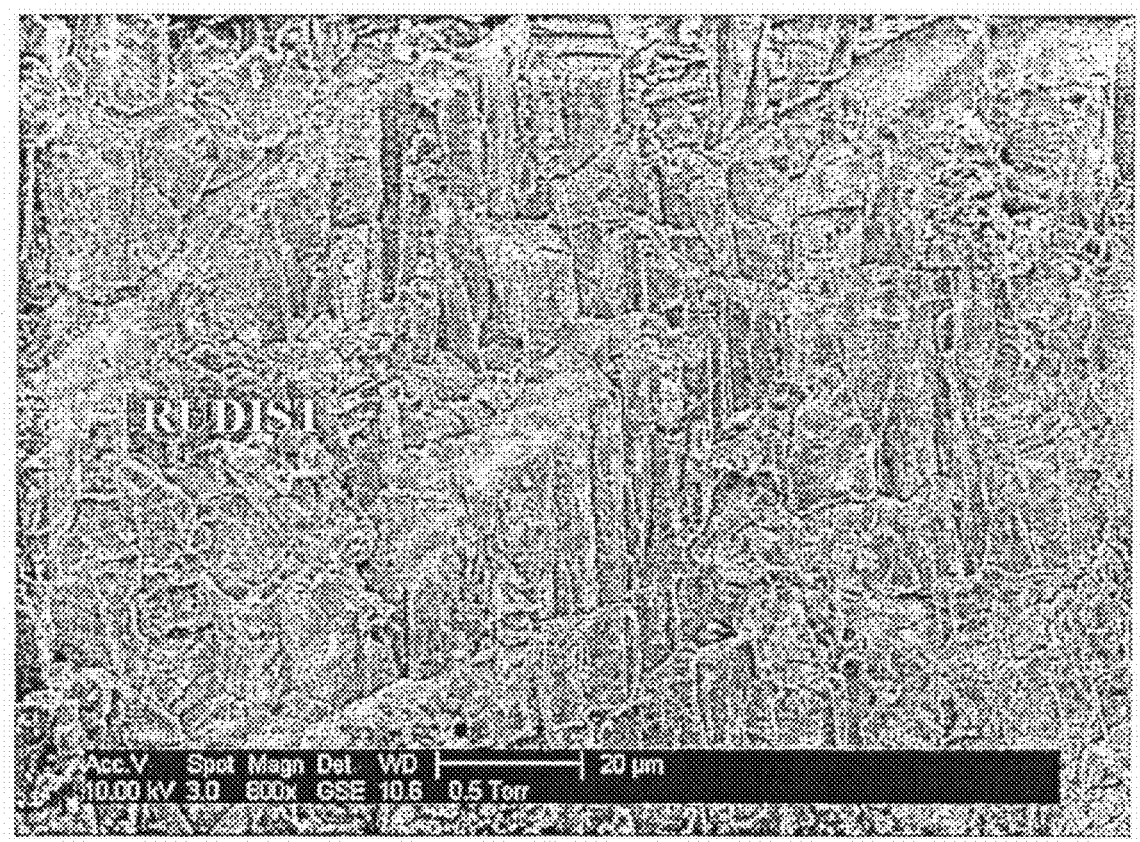
FIG. 4 is a scanning electron microscopic (SEM) image.

In a further step, included within the claims below, Environmental Scanning Electron Microscopy (SEM) was used for the analysis of microporosity within the two different skeletal components of the samples as distinguished by micro-CT. FIG. 3 shows an SEM image of the boundary between a rudist shell fragment and general matrix material. The rudist fragment clearly has lower porosity than the matrix—as shown on the detail in FIG. 4. The porosity distribution below 17 µm resolution was then estimated for these two components using data derived from SEM images.

In combination, these SEM and micro-CT data sets therefore enabled a quantitative estimation of the complete pore shape and size distribution in 3D from micron to centimeter scale. This included the distribution within different components of a carbonate rock and the 3D spatial arrangement of these components.

Figure 5:
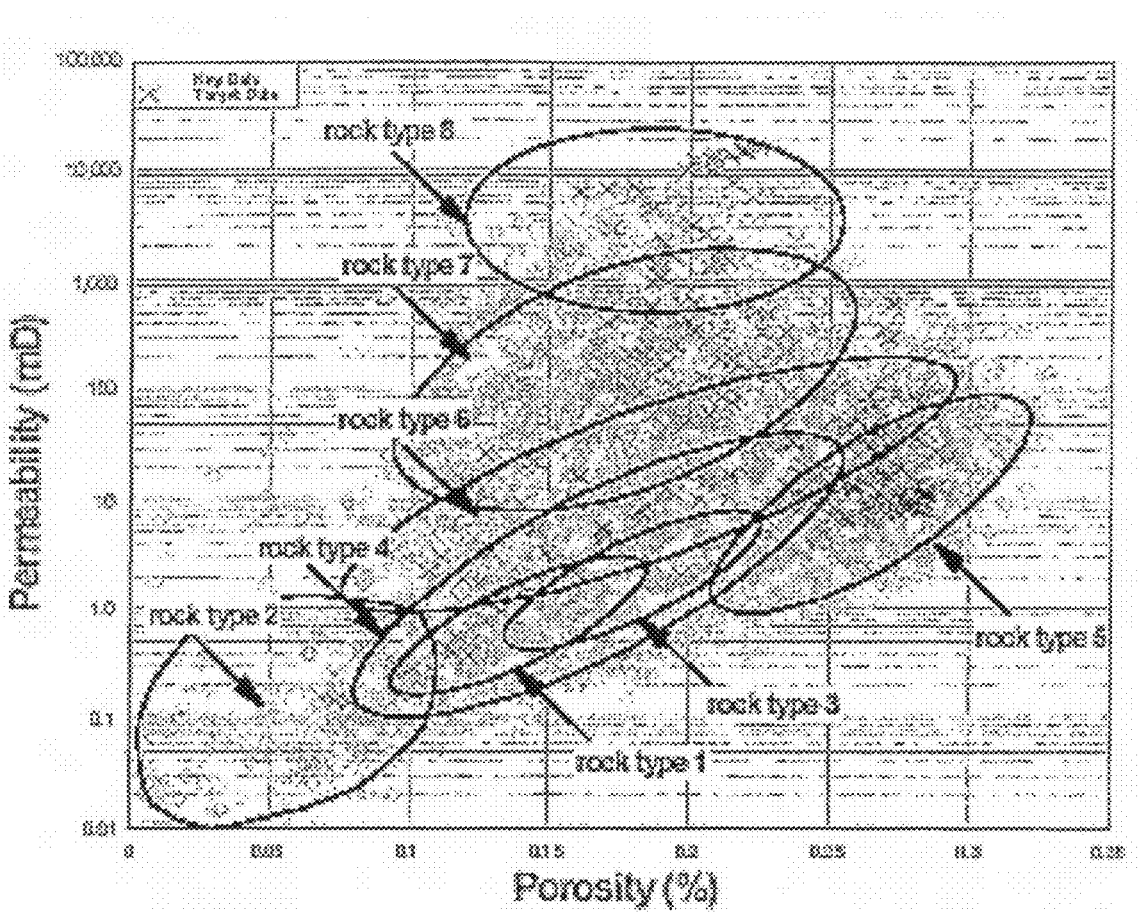
FIG. 5 is a graph correlating permeability with rock types.

With an accurate classification of a sample or its association with a specific rock type, log measurements can be more accurately evaluated, using methods known per se. In FIG. 5, illustrating Step 6 of FIG. 1, there are shown known porosity measurements taken from a wireline logging tool versus formation permeability on a logarithmic scale. Given the knowledge of the rock type, it is possible to estimate the permeability with significantly increased accuracy. For example, in FIG. 5, rock type 3 and rock type 8 share approximately the same porosity range, however, the permeability of the two rock types differs by three orders of magnitude.

These and other known method, as described for example by S. D Russell et. Al. 002. Rock types and permeability prediction from dipmeter and image logs: Shuaiba reservoir (Aptian), Abu Dhabi. AAPG Bulletin, 86 (202), 1709-1732, may be used in combination with the rock type classification.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

The invention claimed is:

1. A method of determining a parameter of interest of a dominantly carbonate rock formation, the method comprising: (a) measuring a tomographic x-ray attenuation or absorption distribution of a sample of said rock formation, the tomographic resolution being chosen so that pore space part or phase is easily distinguishable from the mineral parts or phases;
   (b) identifying a mineral phase part of said distribution; and
      (c) subdividing said mineral phase part of said distribution to derive classification or rock type information of said sample.

2. The method of claim 1 wherein the x-ray attenuation is measured using x-ray tomographic methods of a three dimensional (3D) sample.

3. The method of claim 1 wherein the sample is classified in accordance with statistical data and properties derived from the subdivision of the mineral phase part.

4. The method of claim 1 further comprising the steps of classifying the rock sample and using said classification to analyze log measurements or seismic measurements.

5. The method of claim 1 wherein the parameter of interest is permeability.

6. The method of claim 5 comprising the steps of classifying the rock sample and combining said classification with porosity measurements to determine the permeability of the formation.

* * * * *